United States Patent [19]

Bootman et al.

[11] Patent Number: 4,493,701
[45] Date of Patent: Jan. 15, 1985

[54] WOUND DRAINAGE DEVICE OF RESILIENT SIDEWALLS WITH A CONSTANT RATE OF RECOVERY

[75] Inventors: Matthew W. Bootman, Goleta; Peter Schillke; Stephen W. Laguette, both of Santa Barbara, all of Calif.

[73] Assignee: American Hospital Supply Corporation, Evanston, Ill.

[21] Appl. No.: 409,671

[22] Filed: Aug. 19, 1982

[51] Int. Cl.³ .............................................. A61M 1/06
[52] U.S. Cl. .................................... 604/73; 604/133; 222/567
[58] Field of Search .................... 604/73–75, 604/141, 142, 151, 181, 316, 313, 131–134; 128/DIG. 21, 760, 765–767; 222/567, 569, 570; 141/25, 26, 28; 215/311, 315

[56] References Cited

U.S. PATENT DOCUMENTS

| | | | |
|---|---|---|---|
| 3,084,823 | 4/1963 | Reichstein | 215/311 |
| 3,697,473 | 10/1972 | Blmanteer et al. | 128/DIG. 21 |
| 3,875,941 | 4/1975 | Adair | 141/26 |
| 3,900,029 | 8/1975 | Melnick | 604/133 |
| 4,429,693 | 2/1984 | Blake et al. | 604/133 |

OTHER PUBLICATIONS

Catalog Cut Dow Corning Bulletin: 51–055A, "Silastic Block", Dow Corning, Midland, Michigan 48640, 2 pp., May, 1973.

Primary Examiner—John D. Yasko
Assistant Examiner—J. L. Kruter
Attorney, Agent, or Firm—Roger A. Williams

[57] ABSTRACT

A wound drainage reservoir which is a container having a resilient sidewall that defines a chamber within the container and wherein an opening extends through the sidewall. A helmet extends through the opening, which helmet has an extending lip that engages a portion of the sidewall of the container which surrounds the opening. A collar encircles and is bonded to the helmet for sealing such a portion of the sidewall between the iip of the helmet and the collar. A first inlet is on the helmet to provide a first fluid-flow conduit to the chamber. A second inlet is on the helmet to provide a second fluid-flow conduit to the chamber. A drainage outlet is on the helmet to provide a fluid-flow conduit from the chamber. A plurality of ribs extend laterally along the sidewall.

23 Claims, 6 Drawing Figures

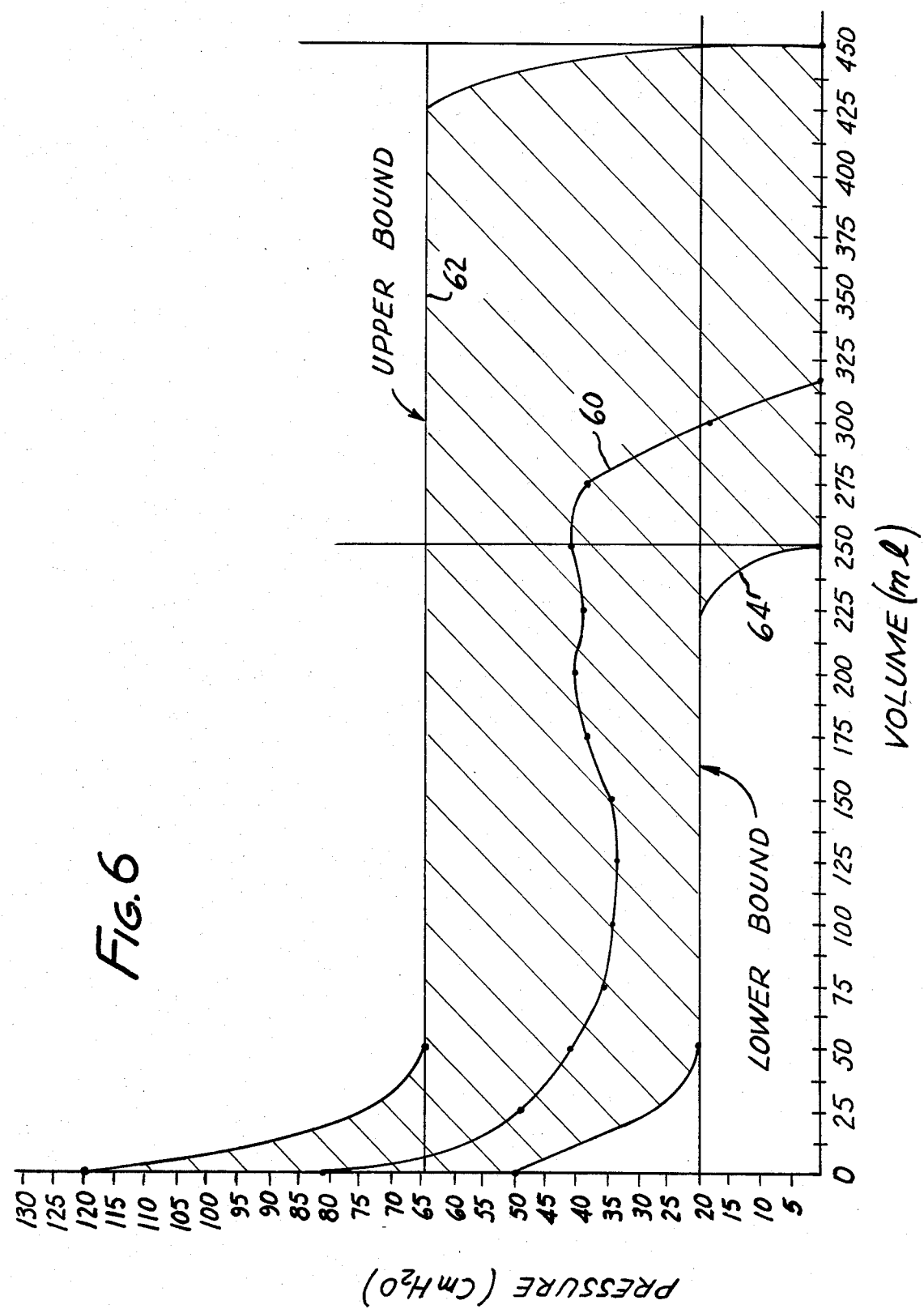

WOUND DRAINAGE DEVICE OF RESILIENT SIDEWALLS WITH A CONSTANT RATE OF RECOVERY

BACKGROUND OF THE INVENTION

The invention herein relates to a disposable wound drainage reservoir having utility in draining fluid from wounds. Primarily, wound drainage reservoirs are used to remove fluids from surgically created wounds. Wound drainage reservoirs are on many occasions utilized following orthopedic surgery, plastic surgery, mastectomies, thoracic and abdominal surgeries.

Many of the currently available wound drainage reservoirs are not disposable, especially wound drainage reservoirs which are used for collecting relatively large volumes of fluid; i.e., 300 ml or more. Such large reservoirs need to be sterilized between uses and thereby provide a source for infection and cross-contamination if complete sterilization is not accomplished.

It would be desirable to have a large volume, disposable, wound drainage reservoir.

SUMMARY OF THE INVENTION

The invention herein is directed to a wound drainage reservoir and in particular, a large volume, disposable, wound drainage reservoir which provides a container having a resilient sidewall which defines the chamber or reservoir within the container. The reservoir is substantially oval in lateral cross section with the ends being somewhat flattened. The sidewall has an opening generally located at one of the ends of the container, through which is mounted a helmet. The helmet portion extends through the opening and has an outwardly extending lip which engages a portion of the interior surface of the sidewall. A collar extends around the portion of the helmet projecting outwardly of the container and is bonded to the helmet in a manner which sandwiches the sidewall between the collar and lip on the helmet, thereby securing the collar, helmet and container together.

A first inlet conduit is provided on the helmet for providing a fluid-flow passageway to the chamber within the container. A second inlet conduit is also provided on the helmet for providing a second fluid-flow passage into the chamber. A drainage connector conduit is attached to the helmet for providing a passage through which the contents once collected in the wound drainage reservoir chamber can be emptied or through which a vacuum can be applied to the chamber to assist in collecting fluid through the inlet conduits.

A plurality of ribs are provided on the sidewall of the wound drainage reservoir. The ribs extend along the sidewall and preferably along the inner surface of the sidewall. Such a plurality of ribs combine with the resiliency of the sidewall to return the container to an uncollapsed state after it has been collapsed.

BRIEF DESCRIPTION OF THE DRAWINGS

The above described features and advantages of the wound drainage reservoir herein will be described with regard to the following detailed description and the accompanying drawings wherein:

FIG. 6 is a graph illustrating the preferred performance band of the wound drainage reservoir herein as a function of pressure and volume.

DETAILED DESCRIPTION

Figure 1:
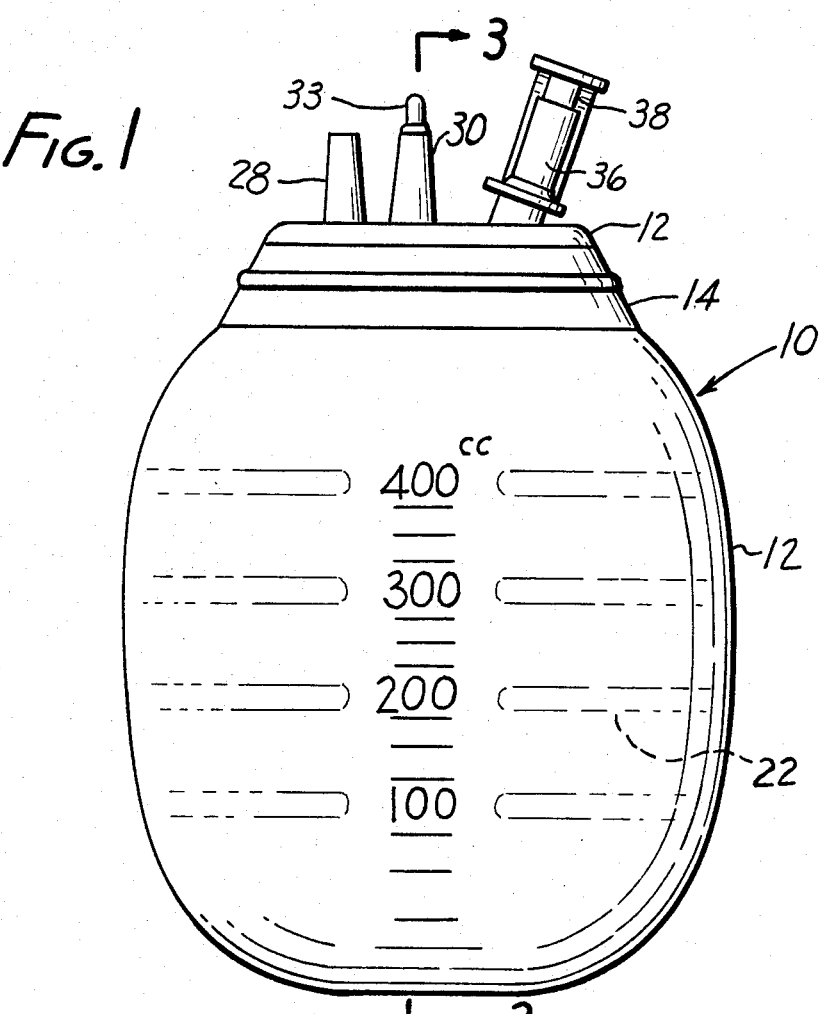
FIG. 1 is a side elevational view of an embodiment of the wound drainage reservoir herein.

The wound drainage reservoir herein will be described with regard to the accompanying drawings. FIG. 1 is a view of an embodiment of a wound drainage reservoir 10. The wound drainage reservoir has a resilient sidewall 12 which defines a chamber 18 within the wound drainage reservoir.

Figure 2:
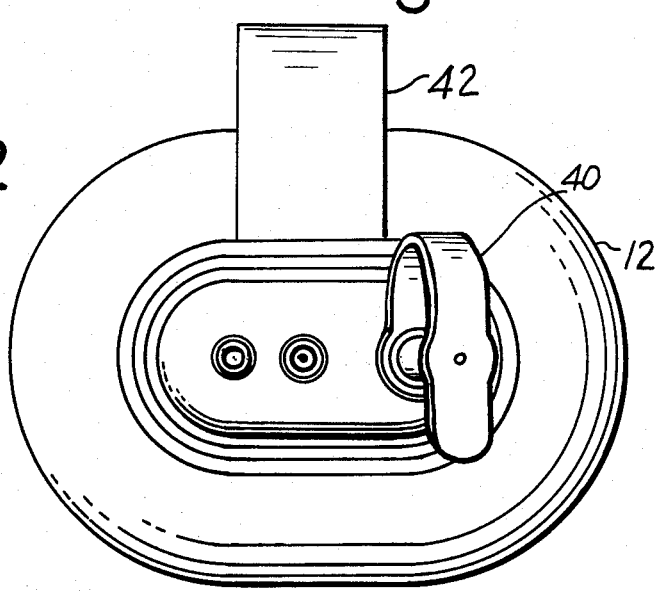
FIG. 2 is a top plan view of the embodiment shown in FIG. 1.

Preferably, the wound drainage reservoir has a configuration as is shown in FIGS. 1 and 2. That is, the lateral cross section of the reservoir is generally oval. A vertical cross section through the reservoir is also generally oval. The bottom of the reservoir can be somewhat flattened in order to provide stability to the reservoir so that it may be set upright on a surface.

The resilient sidewall 12 of the container can be any sufficiently resilient material which when formed into the container 10 as shown provides flexibility to the container such that the container can be collapsed and following such collapse, recovers its original shape. That is, the sidewall can be collapsed upon itself such as through a squeezing action of an operator's hand and following such collapse can recover its original oval cross-sectional shape. Preferably, the sidewall is constructed of a resilient material having a 70 durometer (Shore A). A preferred material for the sidewall is a silicone having a 70 durometer (Shore A). Another consideration for the sidewall material is that the sidewall should be constructed of a material that is substantially inert to the fluid to be collected and generally impervious to the passage of such fluid.

The wound drainage reservoir herein is simply constructed in that it can be constructed of only three parts, namely: the container, formed by the sidewall; a helmet 14; and a collar 16. All three parts can be separately molded and then bonded together in one bonding step.

Figure 3:
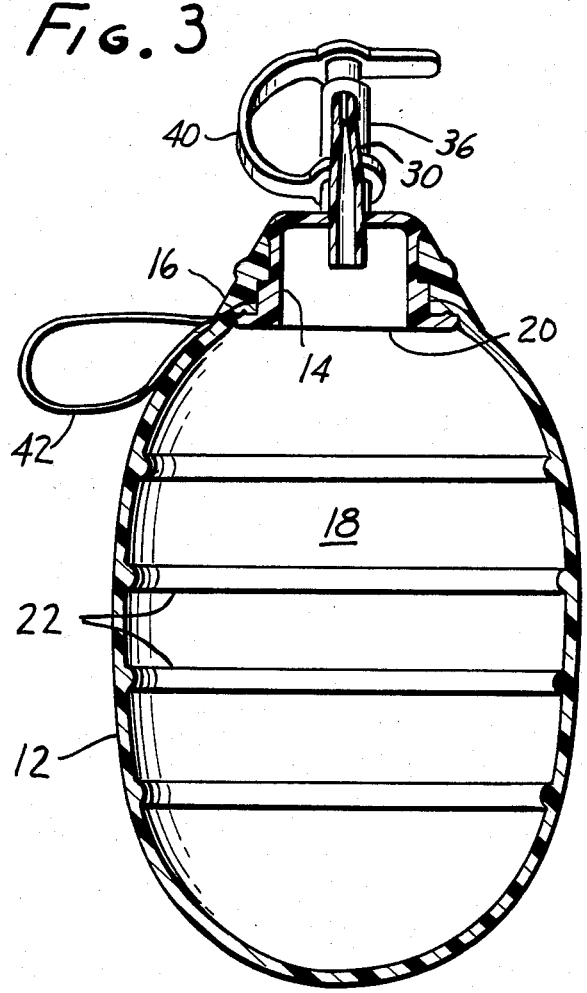
FIG. 3 is a cross-sectional view of the embodiment shown in FIG. 1 taken along the lines 3—3.
Figure 4:
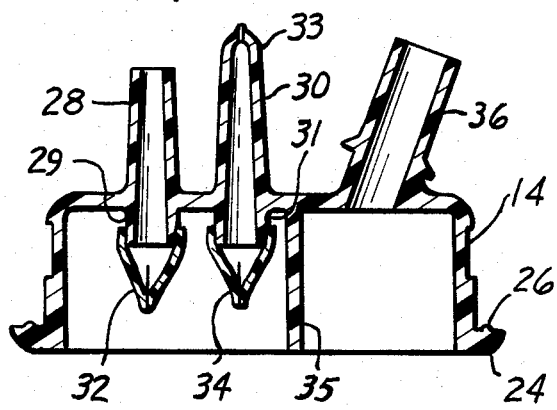
FIG. 4 is a cross-sectional view of an embodiment of the helmet portion of the wound drainage reservoir.
Figure 5:
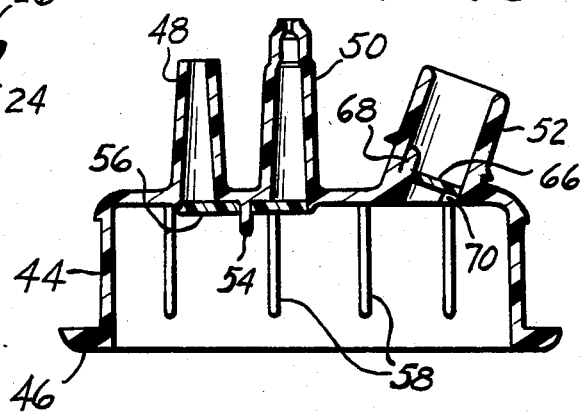
FIG. 5 is a lateral cross-sectional view of another embodiment of a helmet.

The resilient sidewall 12 defines the inner chamber 18 and is provided with an opening 20 which extends through the sidewall, providing access to the inner chamber 18. The helmet 14 extends through the opening 20. The helmet 14 has an outwardly extending lip 24 which is positioned within the chamber formed by the sidewall. The helmet description is better understood with regard to FIGS. 3, 4 and 5. The preferred embodiment of the helmet is shown in FIGS. 3 and 4 and an alternative embodiment of the helmet is shown in FIG. 5. As can be seen with reference to FIGS. 3–5, the helmet extends through the opening 20 and the lip 24 remains within the chamber 18. The upper portion of the helmet extends outwardly of the container. The collar 16 fits over and encircles the upper portion of the helmet. The collar is bonded to the helmet and in bonding the collar to the helmet a portion of the resilient sidewall 12 is sandwiched between the collar and the lip of the helmet. The capture of the portion of the sidewall between the collar and lip forms a seal of the sidewall to the helmet and collar elements.

The outwardly extending lip 24 can be provided with a ridge 26 as is shown in FIG. 4. The ridge 26 projects upwardly from the lip and enhances the seal created between the lip and sidewall.

The helmet is preferably constructed of a harder material than the resilient sidewall. For example, in the preferred embodiment the helmet was constructed of polypropylene. A substantially nonresilient helmet is desirable as the helmet element provides the location for attachment of the wound drainage catheter and, in some instances, a vacuum line. In view of the different hardnesses of the helmet and sidewall, it is desirable to have the helmet constructed as shown in the drawings in order to provide an effective seal between the sidewall and helmet.

The collar portion is preferably constructed of the same material as the helmet. By constructing the collar of the same material, a strong bond can be achieved when the collar is bonded to the helmet during the step of sealing the helmet to the sidewall.

The preferred helmet design is illustrated in FIG. 4. The helmet includes a first inlet conduit 28 which extends outwardly from the upper surface of the helmet. The first inlet conduit is generally cylindrical in shape and provides a passageway therethrough for introducing fluid into the chamber. The first inlet conduit 28 need not project within the helmet, as is shown in the alternative embodiment in FIG. 5. However, it is preferred that a portion 29 of the first inlet conduit project inward of the body of the helmet. It is preferred to have such an inwardly projecting portion 29 so that a first one-way valve 32, such as a miter valve, can be attached to such an inwardly extending portion. A one-way valve permits fluid to enter the reservoir via the first inlet conduit and prevents fluid from leaving through such first inlet conduit.

A second inlet conduit 30 is also provided on the helmet. As with the first inlet conduit 28, the second inlet conduit is generally cylindrical in shape and extends outwardly from the helmet. Again, preferably the second inlet conduit includes a portion 31 which projects inwardly of the helmet. The portion 31 of the second inlet conduit projecting inwardly of the helmet can be provided with a one-way valve 34. Such a one-way valve 34 permits fluid-flow into the reservoir and prevents fluid-flow outwardly of the reservoir through such second inlet conduit.

In the preferred embodiment, at least one of the inlet conduits is provided with a plug or breakway portion 33. A plug is provided which can be readily removed to open the inlet to fluid-flow. Such a plug provides versatility and adaptability to the reservoir. By leaving one inlet conduit plugged or open, the reservoir can be selectively used with one or two drains. As shown in FIG. 4 of the preferred embodiment, the second inlet conduit is provided with a breakaway portion 33 that is integrally molded with the helmet 14. The breakaway portion 33 can be readily broken away from the second inlet conduit to open the conduit to fluid-flow.

The one-way valves 32 and 34 can be any suitable one-way valve. For the preferred embodiment shown in FIG. 4, the one-way valves are miter valves (duckbill-type valves) which extend over the projecting portions 29 and 31 of the first and second inlet conduits.

The miter valves are collapsed tubes which open only when fluid flows therethrough in one direction. An alternative one-way valve system is disclosed with regard to the embodiment shown in FIG. 5. In the embodiment of FIG. 5, the first inlet conduit 48 and second inlet conduit 50 do not extend inwardly of the helmet 44. In such an embodiment, a valve post 54 extends inwardly of the helmet. A resilient valve 56 is positioned around the post so that it covers the passages in the first and second inlet conduits. When no flow is passing through the inlet conduit, the resilient valve 56 remains seated against the passages in the conduits. When a flow is directed through the inlet conduit, the resilient valve opens, permitting the fluid to flow into the reservoir. The resilient valve 56 fits over the passages in the first and second inlet conduits and is thereby seated so as not to open into the conduits themselves. Thus, the resilient valve is a one-way valve preventing fluid-flow from the reservoir outwardly of the inlet conduits 48 and 50.

The one-way valves can be constructed of any sufficiently flexible material to provide the opening and closing capabilities. For example, the one-way valves shown in the embodiments of FIGS. 4 and 5 are preferably constructed of latex.

Also provided on the helmet is a drainage connector 36 (shown as 52 in the embodiment of FIG. 5). The drainage connector is a generally cylindrical conduit extending outwardly from the helmet which provides a passage into the reservoir or chamber 18 of the container. Preferably, the drainage connector 36 does not extend inwardly of the helmet. In this manner, fluid collected in the reservoir can be readily poured from the reservoir by merely tipping the reservoir to permit the fluid to flow through the drainage connector. To enhance the ability to pour collected fluid from the reservoir, the drainage connector 36 can be angled from the helmet as is shown in the drawings. By angling the drainage connector, the collected fluid can be drained from the reservoir readily while minimizing the likelihood of the fluid coming in contact with the inner portions of the first and second inlet conduits.

The drainage connector 36 can also serve as a vacuum connector for providing a vacuum or reduced pressure to the chamber 18 within the container. That is, a vacuum source can be connected through suitable tubing to the wound drainage reservoir by connecting the tubing to the drainage connector 36. In this manner, a vacuum can be applied to enhance drainage of fluid from the wounds.

The drainage connector 36 can be provided with a plug 38 which can be readily removed and inserted to block the drainage connector. For example, a drainage plug 38 can be provided on a plug connector 40 which is essentially a band fastened to the drainage connector. The plug and connector can be integrally molded of any suitable resilient material.

A one-way valve can be provided in the drainage connector to prevent fluid-flow back into the reservoir. Any suitable one-way valve can be used. As shown in FIG. 5, the one-way valve 66 comprises a resilient flap valve which is fitted around a valve post 68 and seats against ledge 70.

It is preferred to have the helmet reinforced by reinforcing elements. That is, during manufacture of the reservoir heat is applied which can have deleterious effects on the helmet portion. Thus, in order to strengthen the helmet, supporting elements are preferably provided. As can be seen in FIG. 4, a preferred support 35 is provided on the helmet which extends across the width of the helmet. An alternative embodiment of such a support is the plurality of support ribs 58 provided in the helmet shown in FIG. 5. The support ribs 58 do not extend completely across the helmet. The reinforcement and supporting ribs are beneficial in that they prevent crazing or cracking of the helmet when the reservoir is assembled or during sterilization.

When the wound drainage reservoir is assembled by bonding the collar and helmet together to sandwich the sidewall and seal the sidewall to the helmet, a strap can also be bonded to the reservoir. For example, a strap 42 can be attached to the reservoir. Such a strap 42 provides a means for supporting the reservoir either on a stand, exterior of a wound dressing, a patient's gown, the bed, or any other convenient location.

Along the inner surface of the sidewall 12 is a plurality of ribs 22. The ribs 22 can extend around the container on such an inner surface. The ribs can be provided on the outer surface of the sidewall, but in the preferred embodiment are preferably on the inner surface. The ribs 22 need not extend completely around the reservoir.

The ribs 22 provide several benefits to the construction of the reservoir. The internal ribs help overcome the problem of crazing, cracking of the sidewall, during repeated use of the reservoir. That is, in use the reservoir is repeatedly collapsed and thereafter allowed to expand in order to draw fluid from the wounds into the reservoir. The internal ribs aid in overcoming such crazing of the sidewall.

The internal rib structure also aids in overcoming structural deformities of the reservoir which can be induced by lengthly activation time associated with slow flow rates. That is, when the reservoir is collapsed and then permitted to expand to draw in fluid, if the fluid-flow rate is sufficiently slow that the reservoir remains substantially collapsed for a unnecessarily long time, structural deformity can occur. The internal rib structure helps overcome the likelihood of such structural deformity occurring. The internal ribs act like springs in returning the sidewall to its original shape. This is accomplished by the internal rib structure providing a relatively constant rate of recovery for the sidewall to its original configuration after having been collapsed. This phenomenon of constant recovery rate is shown in FIG. 6 which is a plot of pressure in centimeters of water versus volume in milliliters. The pressure is the drawing pressure created through the inlet on the reservoir as the reservoir expands to its original shape after having been collapsed. The volume axis is designed for a 450 milliliter reservoir and shows the volume of fluid drawn into the container after having been collapsed to about half of its original volume. The curve 60 shows data collected from a preferred embodiment of the wound drainage reservoir having a capacity of about 400 milliliters. The reservoir was collapsed with a two-handed squeeze until the sidewall was collapsed upon itself. The reservoir was released and allowed to expand. Upon expansion the reservoir drew in water through its inlet. As can be seen from FIG. 6 and the curve 60, during collection of the liquid there was a substantially constant pressure exerted in drawing the liquid into the reservoir up and to about slightly greater than half the total volume of the reservoir. At about that collected volume, the dimples created by collapsing the reservoir essentially disappeared. The curve 62 illustrated in FIG. 6 would be an ideal curve for a 450 milliliter reservoir. That is, the force exerted to draw the liquid into the reservoir would remain substantially constant until the reservoir was substantially full. The curve 64 represents the minimum curve for a 450 milliliter reservoir. That is, it would be preferred to have a wound drainage reservoir which would exceed the standards shown in the curve 64. Basically, such standards are a substantially even draw rate on the fluid, filling pressure, up to at least half the volume of the fluid being collected. Providing the ribs 22 on the internal surface of the sidewall the minimum standards are achieved and overachieved as is shown in FIG. 6.

We claim:

1. A wound drainage reservoir comprising:
   a container having a resilient sidewall defining a chamber within the container, which sidewall includes resilient means for providing a substantially constant rate of recovery for the sidewall to its original configuration after having been collapsed, and an opening extending through the sidewall to the chamber;
   a helmet extending through the opening having an outwardly extending lip extending circumferentially around the helmet, which lip engages an inside surface of a portion of the sidewall of the container which surrounds the opening the helmet further having an indented portion which projects outwardly from the opening;
   a collar means encircling and bonded to a portion of the helmet which projects outwardly from the opening for sealing such portion of the sidewall between the lip of the helmet and such collar means;
   a first inlet means on the helmet for providing a first fluid-flow conduit to the chamber;
   a second inlet means on the helmet for providing a second fluid-flow conduit to the chamber;
   a drainage outlet means on the helmet for providing a fluid-flow conduit from the chamber; and
   a plurality of ribs extending laterally along the sidewall.

2. A wound drainage reservoir as recited in claim 1 wherein the resilient sidewall of the container comprises a material having a durometer of 70 Shore A.

3. A wound drainage reservoir as recited in claim 1 wherein the resilient sidewall comprises silicone.

4. A wound drainage reservoir as recited in claim 1 wherein the helmet comprises a polypropylene helmet.

5. A wound drainage reservoir as recited in claim 4 further comprising an internal rib extending across the helmet for strengthening the helmet.

6. A wound drainage reservoir as recited in claim 1 wherein the lateral extending ribs are integrally molded with the sidewall.

7. A wound drainage reservoir as recited in claim 1 wherein the ribs extend partially around the container and project inwardly.

8. A wound drainage reservoir as recited in claim 1 further comprising a ridge on the lip of the helmet, which ridge engages such portion of the sidewall.

9. A wound drainage reservoir as recited in claim 1 further comprising a one-way valve means in the helmet for permitting fluid-flow into the chamber and preventing fluid-flow out of the chamber through such first and second inlet means.

10. A wound drainage reservoir as recited in claim 9 wherein the one-way valve means comprises a flap valve extending over the openings of the first and second inlet means.

11. A wound drainage reservoir as recited in claim 9 wherein the one-way valve means comprises a miter valve on each of the first and second inlet means.

12. A wound drainage reservoir as recited in claim 1 wherein at least one of the first or second inlet means has a breakaway enclosed end.

13. A wound drainage reservoir as recited in claim 1 further comprising a one-way valve means in the helmet for preventing fluid-flow into the chamber through such drainage outlet means.

14. A wound drainage reservoir as recited in claim 13 wherein such one-way valve means comprises a resilient flap valve, a valve post and a valve seat positioned within the drainage outlet means.

15. A wound drainage reservoir as recited in claim 14 wherein the one-way valve means comprises a miter valve.

16. A wound drainage reservoir comprising:
  a resilient silicone sidewall defining a chamber therewithin and which sidewall includes resilient means for providing a substantially constant rate of recovery for the sidewall to its original configuration after having been collapsed and having an opening extending therethrough;
  a helmet extending through the opening having an outwardly extending lip extending circumferentially around the helmet upon which is provided a ridge, which lip and ridge engage an inside surface of a portion of the sidewall;
  a collar encircling and bonded to a portion of the helmet which project outwardly from the opening which sandwiches a portion of the sidewall between the lip of the helmet and the collar;
  a first inlet conduit generally cylindrical in shape which extends from the helmet to provide a first fluid-flow conduit to the reservoir;
  a second inlet conduit generally cylindrical in shape extending from the helmet to provide a second fluid-flow conduit to the reservoir;
  a drainage outlet generally cylindrical in shape extending from the helmet to provide a fluid-flow conduit from the reservoir;
  a plurality of ribs on an inner surface of the sidewall within the reservoir which extend laterally along the sidewall;
  a first one-way valve on the first inlet conduit which permits fluid-flow into the reservoir; and
  a second one-way valve on the second inlet conduit which permits fluid-flow into the reservoir.

17. A wound drainage reservoir as recited in claim 1 or 16 wherein the reservoir has a volume of about 400 ml.

18. A wound drainage reservoir as recited in claim 1 or 16 wherein the sidewall has a resiliency sufficient to provide upon collapsing and subsequent recovery of its original shape a substantially constant pressure intake through such inlet conduits up to a collected liquid volume of about one-half the total volume of such reservoir.

19. A wound drainage reservoir as recited in claim 1 or 16 wherein the resilient means included on the sidewall has a sufficient resiliency such that the reservoir exhibits an intake pressure after collapse of the sidewall and subsequent return to its original shape of about 20 cm. of water to about 65 cm. of water.

20. A wound drainage reservoir as recited in claim 20 wherein the resilient means included on the sidewall provides such intake pressure at least up to collection of a volume of liquid about one-half the total volume of the reservoir.

21. A wound drainage reservoir comprising:
  a container having a resilient sidewall defining a chamber within the container and an opening extending through the sidewall to the chamber;
  a helmet extending through the opening having an outwardly extending lip extending circumferentially around the helmet, which lip engages an inside surface of a portion of the sidewall of the container which surrounds the opening;
  engagement means on the lip of the helmet for engaging a portion of the sidewall;
  a collar encircling and bonded to a portion of the helmet which projects outwardly from the opening for sealing such portion of the sidewall between the engagement means on the lip of the helmet and such collar means;
  a first inlet means on the helmet for providing a first fluid-flow conduit to the chamber;
  a second inlet means on the helmet for providing a second fluid-flow conduit to the chamber;
  a drainage outlet means on the helmet for providing a fluid-flow conduit from the chamber; and
  a plurality of ribs extending laterally along the sidewall.

22. A wound drainage reservoir as recited in claim 21 wherein the sidewall has a resiliency sufficient to provide a constant rate of recovery of its original configuration after having been collapsed.

23. A wound drainage reservoir as recited in claim 21 wherein the engagement means comprises a ridge on the lip of the helmet, which ridge engages such portion of the sidewall.

* * * * *

UNITED STATES PATENT AND TRADEMARK OFFICE
CERTIFICATE OF CORRECTION

PATENT NO. : 4,493,701
DATED : January 15, 1985
INVENTOR(S) : Matthew W. Bootman; Peter Schillke; Stephen W. Laguette It is certified that error appears in the above-identified patent and that said Letters Patent are hereby corrected as shown below:

Column 8, line 14, change "20" to -- 19 --.

Column 8, line 45, change "of" to -- to --.

Signed and Sealed this

Twenty-first Day of May 1985

[SEAL]

Attest:

DONALD J. QUIGG

Attesting Officer     Acting Commissioner of Patents and Trademarks